(12) United States Patent
Chahine et al.

(10) Patent No.: US 6,221,260 B1
(45) Date of Patent: Apr. 24, 2001

(54) SWIRLING FLUID JET CAVITATION METHOD AND SYSTEM FOR EFFICIENT DECONTAMINATION OF LIQUIDS

(75) Inventors: Georges L. Chahine, Silver Spring; Kenneth M. Kalumuck, Columbia, both of MD (US)

(73) Assignee: Dynaflow, Inc., Fulton, MD (US)

( * ) Notice: Subject to any disclaimer, the term of this patent is extended or adjusted under 35 U.S.C. 154(b) by 0 days.

(21) Appl. No.: 09/285,818

(22) Filed: Apr. 2, 1999

(51) Int. Cl.$^7$ ................................. C02F 1/00; C02F 1/02; C02F 1/32; F15D 11/02
(52) U.S. Cl. ..................... 210/748; 210/749; 210/764; 210/765; 210/766; 210/774; 210/787; 210/175; 210/198.1; 210/206; 210/220; 210/512.1; 239/251; 239/399; 239/487
(58) Field of Search ..................... 210/748, 749, 210/764, 760, 765, 774, 175, 787, 198.1, 206, 220, 512.1; 239/399, 487, 251

(56) References Cited

U.S. PATENT DOCUMENTS

| | | |
|---|---|---|
| 1,508,281 | 9/1924 | Kelly . |
| 1,575,671 | 3/1926 | Beanes . |
| 2,428,748 | 10/1947 | Barz . |
| 3,528,704 | 9/1970 | Johnson, Jr. et al. . |
| 4,076,617 | 2/1978 | Bybel et al. . |
| 4,262,757 | 4/1981 | Johnson, Jr. et al. . |
| 4,389,071 | 6/1983 | Johnson, Jr. et al. . |
| 4,474,251 | 10/1984 | Johnson, Jr. et al. . |
| 4,508,577 | 4/1985 | Conn et al. . |
| 4,610,321 | 9/1986 | Whaling . |
| 4,681,264 | 7/1987 | Johnson, Jr. et al. . |
| 4,906,387 | 3/1990 | Pisani . |
| 4,990,260 | 2/1991 | Pisani . |
| 5,086,974 | 2/1992 | Henshaw . |
| 5,106,022 | 4/1992 | Pook . |
| 5,154,347 | 10/1992 | Vijay . |
| 5,198,122 | 3/1993 | Koszalka et al. . |
| 5,217,163 | 6/1993 | Henshaw . |
| 5,326,468 | 7/1994 | Cox . |
| 5,393,417 | 2/1995 | Cox . |
| 5,431,346 * | 7/1995 | Sinaisky ................................ 239/399 |
| 5,494,585 | 2/1996 | Cox . |
| 5,749,384 | 5/1998 | Hayashi et al. . |
| 5,984,670 | 11/1999 | McMillan et al. . |

OTHER PUBLICATIONS

Kalumuck et al., "The Use of Cavitating Jets to Oxidize Organic Compounds in Water," Proceedings of FEDSM '98, 1998 ASME Fluids Engineering Division Summer Meeting, Jun. 21–25, 1998, Washington, D.C.

\* cited by examiner

Primary Examiner—David A. Reifsnyder

(57) ABSTRACT

The invention is directed to a high efficiency method for the remediation of large quantities of liquids, operating at low to moderate ambient pressures, in order to reduce environmental or health risks or to purify the liquid for use in industrial processing. Decontamination is achieved through the use of a swirl chamber in which a central vortex is formed which has a core pressure lower than the vapor pressure of the liquid thus inducing cavitation pockets in the vortex, which are then ejected from the nozzle through the exit orifice into a volume of liquid where the cavitation pockets collapse. These cavitation events drive chemical reactions, by generating strong oxidants and reductants, efficiently decomposing and destroying contaminating organic compounds, as well as some inorganics. These same cavitation events also physically disrupt or rupture the cell walls or outer membranes of microorganisms (such as *E. coli* and salmonella) and larvae (such as Zebra mussel larvae), leaving the inner cellular components susceptible to oxidation.

21 Claims, 9 Drawing Sheets

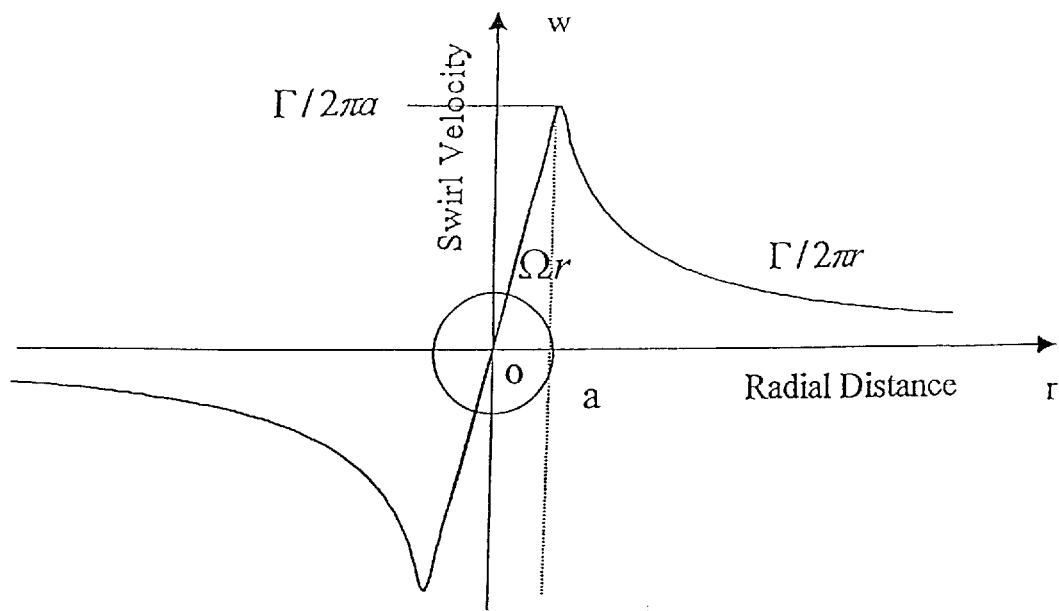
FIG 1.1 DISTRIBUTION OF TANGENTIAL VELOCITY, w
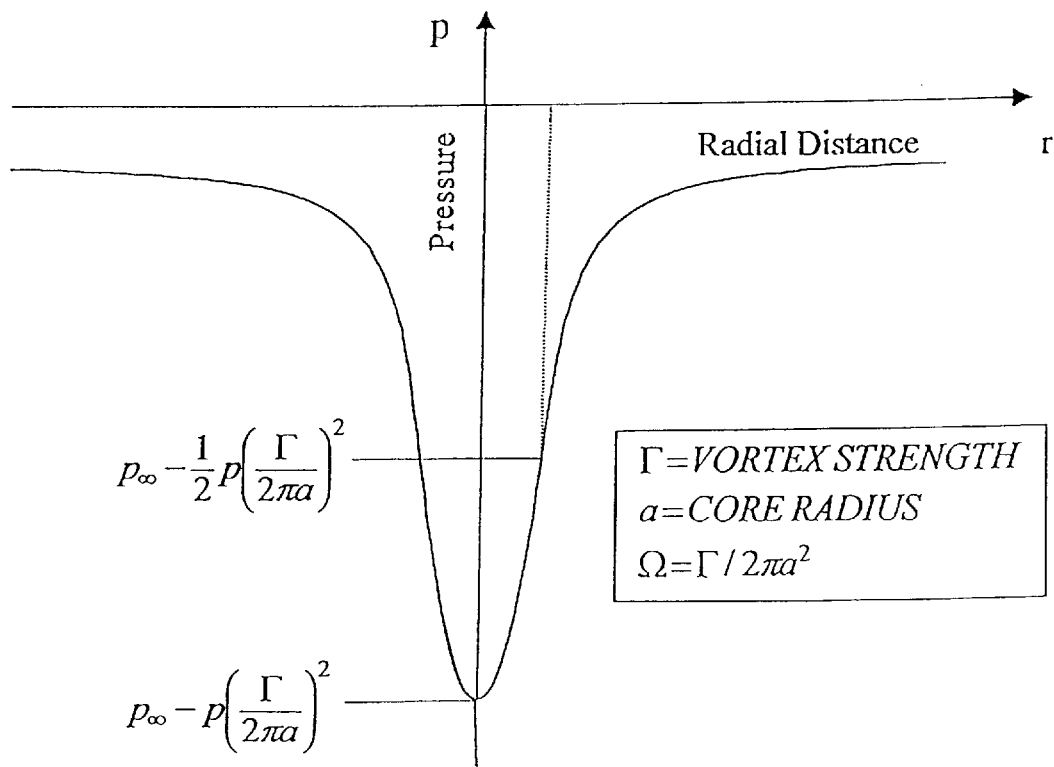
FIG 1.2 DISTRIBUTION OF PRESSURE

SWIRLING FLUID JET CAVITATION METHOD AND SYSTEM FOR EFFICIENT DECONTAMINATION OF LIQUIDS

BACKGROUND OF THE INVENTION

As the environmental, health and industrial impact of pollutants increases, it is becoming increasingly important to develop new methods for the rapid and efficient removal of a wide range of contaminants from polluted waters and other liquids. The invention is directed to a high efficiency method for the remediation of large quantities of liquid, operating at low to moderate ambient pressures, in order to reduce environmental or health risks or to purify the water for use in industrial processes. Moreover, this method reduces or eliminates the use of chemical additives. Rather, decontamination is achieved through the use of submerged liquid jets which trigger hydrodynamic cavitation events in the liquid. These cavitation events drive chemical reactions, by generating strong oxidants and reductants, efficiently decomposing and destroying contaminating organic compounds, as well as some inorganics. These same cavitation events both physically disrupt or rupture the cell walls or outer membranes of microorganisms (such as *E. coli* and *salmonella*) and larvae (such as Zebra mussel larvae), and also generate bactericidal compounds, such as peroxides, hydroxyl radicals, etc., which assist in the destruction of these organisms. Following disruption of the cell wall or outer membrane, the inner cellular components are susceptible to oxidation.

There are many means for removing contaminants and inclusions from liquids, including filtration, stripping, adsorption, absorption, and ion exchange. One technique employs oxidation of contaminants, in which chemical reactions are induced with oxidization agents to break the compounds down into simpler substances which, in turn, may also be oxidized. In the case of organic contaminants, the ultimate end products of oxidation reactions are typically nontoxic substances such as water and carbon dioxide. Thus, oxidation may completely destroy the contaminating substances, rather than merely removing them from the water for disposal elsewhere.

Oxidation reactions may be induced by a variety of means, such as the use of various chemicals, ozone, or supercritical water, or photochemical oxidation where ultraviolet radiation is used to produce hydroxyl radicals, which are strong oxidizing agents. These methods are often costly. Oxidation reactions also can be initiated by inducing hydrodynamic cavitation events in the solution, that is, by inducing the growth and rapid collapse of cavitation bubbles (also called cavities, microcavities or microbubbles) in the liquid. According to one theory, the generation of a "hot spot" (a local high temperature and pressure region) upon cavity collapse is responsible for dissociating the water molecules in aqueous liquids to produce hydroxyl radicals. Other oxidizing radicals may be formed in aqueous solutions as well as in non-aqueous environments. Oxidation reactions thus occur at the site of the collapsing cavity or bubble.

Systems using ultrasonically-induced cavitation have been found to promote a wide range of physical and chemical reactions and to be capable of at least partially oxidizing dilute aqueous mixtures of organic compounds. This may be achieved using ultrasonic horns to send a high intensity acoustic beam into the solution and excite microcavities. U.S. Pat. No. 4,076,617 (Bybel et al.) utilizes cavitation induced by acoustic means to create an emulsion of the waste material in water followed by application of ozone to oxidize the emulsified waste. U.S. Pat. No. 5,198,122 (Koszalka et al.) teaches the application of ultrasonic energy to contaminated liquids in the presence of oxidants. However, the efficiency of such ultrasonic devices is limited by achieving cavitation in the form of a cloud of cavitation bubbles only in a relatively small region near the surface of the ultrasonic source. Moreover, the efficiency of transfer of electric power into ultrasonic energy and then into the liquid itself is quite low, of the order of about 15%.

Other methods employ venturi flow to induce cavitation in contaminated aqueous solutions by relying on the pressure drop and subsequent pressure rise associated with flow through the venturi to cause cavitation bubble nuclei to grow and collapse. However, these methods are limited by their complexity and efficiency, and may require additional treatments, such as with chemical oxidizing agents, ultraviolet radiation, or both, to achieve the desired water purity. U.S. Pat. No. 4,906,387 (Pisani) and U.S. Pat. No. 4,990,260 (Pisani) teach first inducing cavitation in contaminated water which has been treated to provide hydroxyl free radicals and then irradiating the cavitated treated water with ultraviolet radiation. Cavitation is induced by passing the water through a cavitation critical flow constriction, shown in the figures to be a venturi-type constriction (that is, a cylindrical conduit of gradually decreasing and then gradually increasing inner diameter).

U.S. Pat. No. 5,326,468, U.S. Pat. No. 5,393,417, and U.S. Pat. No. 5,494,585 (the Cox patents) teach the production of oxidation by action of a cavitation venturi which is operated with a throat size and pressure drop to incur cavitation in the water. The Cox cavitation venturi comprises an inlet passage which converges in a cone, and a variable throat which is controlled by feedback from various sensors. The cavitation phenomenon which results in the formation and collapse of micro-bubbles is said to be contained in the expanding diameter outlet body of the venturi, the large end of which is essentially the same diameter as the inlet passage to the venturi. Sensors and programmable control feedback are used to adjust the throat of the venturi nozzle to optimize cavitation conditions. Oxidation is continued by the use of high energy ultraviolet radiation and/or hydrogen peroxide injection. The cavitation taught by Cox requires high velocities and energy in order for cavitation to occur as a result of the pressure drop generated in the liquid.

Submerged jet nozzles have been used to generate a highly concentrated and focused stream of cavitation in various fluids for the purpose of mechanically eroding, cutting, cleaning, or drilling into solid surfaces. See, for example, U.S. Pat. No. 4,508,577 (Conn et al.), U.S. Pat. No. 4,262,757 (Johnson et al.), U.S. Pat. No. 4,389,071 (Johnson et al.), U.S. Pat. No. 4,474,251 (Johnson et al.), U.S. Pat. No. 4,681,264 (Johnson et al.) and U.S. Pat. No. 3,528,704 Johnson, Jr.) which describe various fluid jets and their use for drilling, cleaning, cutting, and the like.

U.S. Pat. No. 3,528,704 discloses cavitating nozzles that utilize stem members of various configurations centrally positioned within the restricted orifice to further increase the velocity of the stream as it passes through the orifice. Additionally, as the stream passes over the stem member an evacuated core area is described as being formed which further reduces the pressure within the stream thus enhancing the formation of cavitation bubbles. One embodiment describes positioning flow rotating stator vanes within the nozzle chamber to impart a vortex movement to the stream as it leaves the nozzle. The nozzles described in this reference are taught to be useful in various drilling applications. U.S. Pat. No. 5,086,974 (Henshaw) decribes a cavitating jet nozzle for cleaning surfaces, which includes a free-floating pin received at a central position which lowers the pressure such that cavitation bubbles form in the liquid.

The use of rotating jet nozzles for cleaning and maintenance purposes is disclosed in U.S. Pat. No. 5,749,384 (Hayasi, et al.) and U.S. Pat. No. 4,508,577 (Conn et al.). The apparatus of Hayashi employs a driving mechanism capable of causing the jet nozzle itself to travel upward-and-downward, to rotate and swing. Conn et al. describe the rotation of a cleaning head including at least two jet forming means, for cleaning the inside wall of a conduit. Neither reference teaches or suggests rotational or swirling motion of the fluid jet itself.

U.S. Pat. No. 4,389,071 and 4,474,251 describe methods and apparatuses for oscillating the velocity of the liquid jet at a preferred Strouhal number within the range of about 0.2 to about 1.2. Such oscillation of the liquid jet is described as advantageously inducing a series of discrete vortices wherein cavitation occurs.

Each of the prior art methods and apparatuses for forming cavitating liquid jets require relatively high inlet pressures into the nozzles to induce cavitation in the liquid stream as it is ejected through the restricted orifices of the cavitating nozzle. The relatively high inlet pressures required in these prior art cavitating nozzles increases power consumption and limits the use of such cavitating nozzles to applications having a readily available source of high pressure fluid.

The present invention achieves increased oxidation by employing a mechanism for generating cavitation in the bulk of the liquid utilizing one or more swirling cavitating liquid jets which achieve cavitation at very high cavitation numbers. This enables maximization of the surface area of the cavities generated and of the volume of liquid subjected to cavitation and minimization of the power input required. This process can be made very efficient and also benefits from the fact that pumps are quite efficient in converting electric (or other) power into hydraulic power. Such a technology could be used for treatment of polluted water, groundwater, wastewater, industrial process water, and drinking water. It could be employed as a stand-alone process or as a part of a treatment train.

BRIEF SUMMARY OF THE INVENTION

The present invention utilizes swirling jet-induced cavitation to efficiently reduce or eliminate contaminants in large volumes of liquid. Very intense cavitation occurs at the center of the rotating flow, and in the shear zone of the jet-like liquid ejected from the nozzle, triggering oxidation and reduction reactions which result in decomposition of contaminating compounds, and also triggering the physical destruction and decomposition of microorganisms and larvae, efficiently and effectively remediating polluted waters or other liquids. As used herein, the term "liquid" is used to indicate any aqueous or non-aqueous liquid or solution comprising one or more contaminants susceptible to destruction or decomposition by the occurrence of swirling jet-induced cavitation events.

It is an object of this invention to provide a method and apparatus for the remediation of aqueous solutions by the generation of aggressive swirling fluid jet cavitation by the steps of: injecting the liquid into a chamber having a longitudinal axis, and swirling the injected liquid about the longitudinal axis to form a central vortex having a core pressure lower than the vapor pressure of the injected liquid to induce a single long or many cavitation pockets in the vortex. The swirling liquid with the cavitation pockets formed in the vortex thereof is then ejected through an exit orifice aligned with longitudinal axis, into a volume of relatively stationary liquid. The shear between the ejected liquid and the stationary liquid produces a multitude of additional bubbles or cavities. It is a closely related object to employ a decontamination system utilizing a multiplicity of such swirling fluid jets.

Preferably, the method for forming a cavitating rotating (or swirling) liquid jet according to the present invention includes the substep of tangentially directing the liquid into the chamber along at least a portion of the longitudinal axis to create the swirling vortex, and may include the further step of sheathing the ejected swirling liquid in an annulus of liquid flowing axially relative to the longitudinal axis.

In a further embodiment of the method of the present invention, a portion of the injected liquid is directed axially into the chamber along the longitudinal axis thereof. In this manner, the axial velocity component of the liquid in the chamber is increased so as to propel the swirling vortex and the cavitation pockets formed therein further from the exit orifice.

A further object is to provide a method and apparatus for decontamination of polluted liquids in which the dynamics of the jet-induced cavitation are optimized for particular contaminants through control of the temperature, pH, ambient pressure, cavitation number, air or other gas content, and/or cavity surface area.

An additional advantage of this invention is that it provides an effective decontamination method that is relatively simple to scale up and adapt to a wide range of industrial and municipal applications, with the related ability to process large quantities of liquids while operating at low to moderate ambient pressures, for modest power consumption.

It is a related object to utilize the dual cavitational effects of the swirling jet nozzle to cause the physical destruction of microorganisms or larvae by disruption of their cell walls or outer membranes and also to cause the chemical oxidation or reduction of organic and some inorganic contaminants, including the cellular components of destroyed microorganisms or larvae.

In an alternative embodiment of the invention, it is intended to provide a remediation method and apparatus in which the cavities are made to collapse more strongly by providing a solid surface in close proximity to the jet flow exiting the nozzle. The presence of the solid surface creates an area of stagnation, promoting asymmetric cavity collapse with the formation of high speed microjets traveling through the collapsing bubbles, intensifying bubble collapse.

Other objects and advantages will become apparent from a consideration of the ensuing description, claims, and accompanying drawings.

BRIEF DESCRIPTION OF THE DRAWINGS

The accompanying drawings, which are incorporated in and constitute a part of the specification, illustrate preferred embodiments of the invention and, together with the general description given above and the detailed description of the preferred embodiments given below, serve to explain the principles of the invention.

FIGS. 1.1 and 1.2 are diagrams graphically illustrating the distribution of tangential velocity and pressure associated with a vortex;

DETAILED DESCRIPTION OF THE INVENTION

Figure 2:
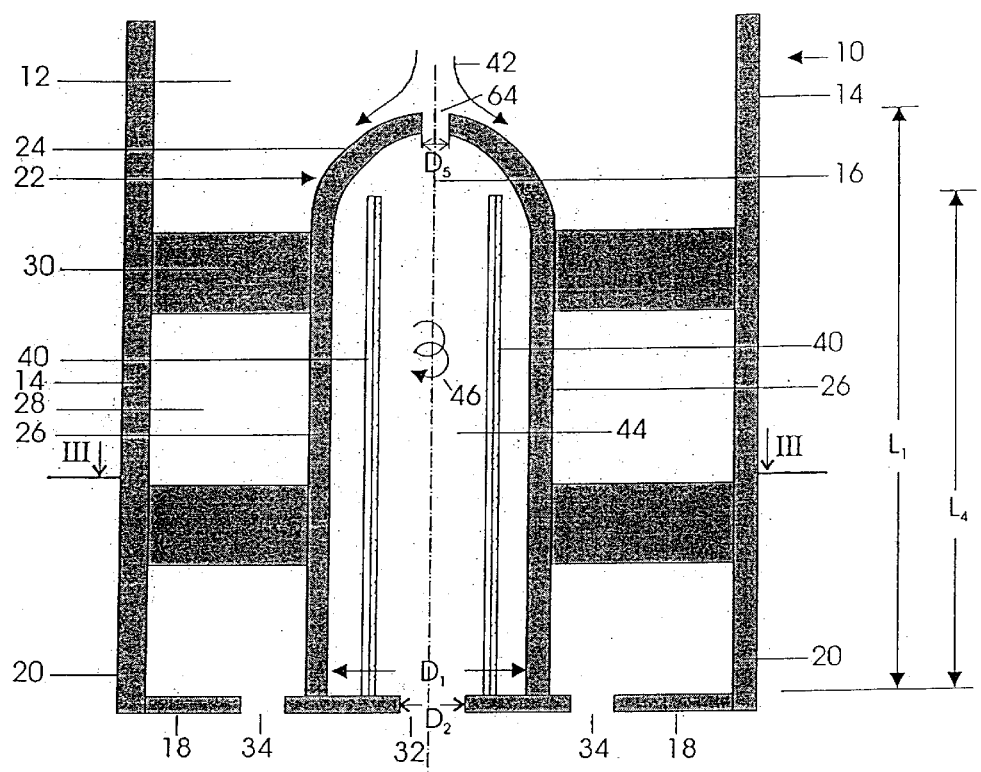
FIG. 2 is a cutaway side view of a first embodiment of a nozzle incorporating the teachings of the present invention.

The detailed elements and specific embodiments of the present decontamination system can be best appreciated by further understanding the cavitation phenomenon employed to drive the physical and chemical decontamination reactions. Due to large pressure drop in a swirling or rotating flow, initially-microscopic bubbles grow in the regions of pressure drop and collapse in the regions of pressure rise. When subjected to cavitation, various molecules in the liquid undergo dissociation and form free radicals which are powerful oxidizing or reducing agents. For example, in aqueous liquids it is believed that the dissociation of water to form hydroxyl radicals occurs under intense cavitation due to the growth and collapse of microscopic bubbles. Analogous dissociation of other molecules may occur as a result of cavitation in aqueous solutions as well as in non-aqueous liquids and solutions, producing radicals which similarly aid in the decontamination reactions described herein. Moreover, cavitation generated in any liquid environment will result in the physical disruption of contaminants, without regard to the generation of particular radicals. The methods and systems of this invention will be applicable for all liquid environments comprising contaminants susceptible to decomposition via the physical and/or chemical effects of the jet cavitation employed.

Jet cavitation refers to the formation and growth of vapor-filled cavities in a high velocity flowing stream of liquid issuing from a suitable nozzle, where the local pressure surrounding the gas nuclei in the liquid is reduced below the pressure necessary for the nuclei to become unstable, grow and rapidly form large vapor-filled cavities or bubbles. This critical pressure is equal to or less than the vapor pressure of the liquid. These vapor-filled cavities are convected along with the jet stream issuing from the nozzle and when the local pressure surrounding the cavities rises sufficiently above the vapor pressure of the liquid, the cavities collapse and chemical reactions occur in the vicinity of the collapse.

There are several theories for the cause of the chemical reactions that take place upon the bubble collapse. According to one, the generation of a "hot spot" upon bubble collapse (local high temperature and pressure region) is responsible for the enhanced reactions. According to this theory, the collapse of the myriad of bubbles in the cavitated region creates a multitude of localized high temperature and high-pressure spots (up to 5,000° C. and 1,000 atmospheres) that achieve the oxidation (and/or reduction) and thus the desired remediation effects. Other theories of cavitation suggest that the reactions are generated by shock waves or electric discharges generated at the bubble collapse, or to the formation of a plasma-like state in the collapsing bubble. Regardless of causation, the physical and chemical reactions that take place at the site of the cavitation event are efficiently utilized in the process of the present invention for the elimination of organic and other contaminants from the liquids.

The characteristics and behavior of the generated cavities strongly affect oxidation efficiency. Due to the low pressures generated at the center of the swirl chamber, aggressive cavitation can be generated at moderate jet pressures with no need to reduce the ambient pressure (for purposes of this invention, "ambient pressure" refers to the pressure of the liquid into which the fluid jet issues). In operation at low to moderate ambient pressures (i.e., about 0 to 100 psi), the swirling fluid jet cavitation used in this remediation method nevertheless generates high volumes of small cavities or cavities whose morphology exhibits a large surface area to volume ratio (e.g., very elongated bubbles, helical patterns, etc.).

It is expected that the cavitational decontamination process of this invention will be operable over a very wide range of pressures. Thus, the system can be utilized in decontaminating the liquids in situ, without the need for removing them or for increasing or reducing the pressure (for example, in industrial processes operating at increased pressures, or in decontaminating polluted waters at depths which result in increased pressures. Nevertheless, from a purely economic standpoint, it would be advantageous to operate at low to moderate ambient pressures for attaining high levels of decontamination while realizing the economies of these lower pressures.

The swirling jet flow nozzles or chambers described here are particularly suitable for use in liquid remediation systems since they generate very intense cavitation-induced oxidation (or reduction) reactions over a large volume of liquid. The use of submerged jet nozzles is preferred, in which the fluid jets into a volume of relatively static aqueous liquid, forming additional vortices in the shear layer in a second shear zone, thereby further increasing the overall cavity surface area.

The surface area of the cavities generated and the surface area-to-volume ratio are key parameters affecting the efficiency of the process, with larger surface areas and surface area-to-volume ratio resulting in higher decontamination efficiencies. This can be explained by the need to bring molecules of the contaminants to be oxidized (or reduced) into close proximity with the hydroxyl radicals, or high pressure and temperature regions, generated by the collapsing cavities. Increasing the overall cavity surface area in contact with the contaminated liquid increases the probability of the hydroxyl radicals and contaminants being close enough to react.

The ability of the swirling jet nozzles to generate cavitation in a large area on the swirl axis and in the shear layer of the exiting jet, and the use of multiple, submerged jet nozzles can be employed to induce very large total cavity surface area-to-volume ratios. Thus, the invention teaches how to employ swirling liquid jet flows to generate widespread and intense cavitation events, producing free radicals that rapidly oxidize organic compounds and ultimately break them down into simple nontoxic compounds such as carbon dioxide and hydrogen. This results in a very high efficiency cavitation-based decontamination system. One can appreciate how the present invention achieves increased decomposition of contaminants by maximizing the surface area of the cavities generated and also maximizing the volume of liquid which is subjected to cavitation. Combined with the ability to operate at a greatly reduced velocities and thus flow rates as compared to prior art methods, the present invention offers a simple and economic system for decontamination of polluted waters and other liquids.

A swirling fluid jet may be formed at relatively high cavitation numbers by positioning chamber means within the external sidewalls of a nozzle for swirling liquid which enters the nozzle about a longitudinal axis passing through the center of the nozzle to thereby form a central vortex within the swirling liquid which has a core pressure lower than the vapor pressure of the liquid to induce cavitation pockets to form in the vortex.

Numerous modifications may be made to the nozzle, however, the underlying concept common to each of the embodiments described herein resides in forming a swirling vortex within the nozzle to thereby induce cavitation within the vortex at relatively low inlet pressures as compared to prior art cavitating nozzles. Alternatively, the invention as embodied herein provides a method and apparatus for forming a cavitating liquid jet at relatively high ambient pressures or low inlet pressures which heretofore had only been possible with exceptionally high inlet pressures into the nozzle thereby resulting in increased consumption of energy and other limitations with regard to the structure of the nozzles to withstand the high inlet pressures. In one embodiment, the invention employs a swirling liquid jet nozzle comprising: an inlet port, and external cylindrical sidewall having a longitudinal axis there through, a first endwall extending inwardly from a distal end of the external cylindrical sidewall, and a first exit orifice aligned on the longitudinal axis. The nozzle of such embodiment further includes chamber means, positioned downstream of the inlet port within the external cylindrical sidewall of the nozzle, for swirling liquid about the longitudinal axis to form a central vortex having a core pressure lower than the vapor pressure of the liquid to induce formation of cavitation pockets in the vortex.

Preferably, the chamber means comprises a hollow streamlined swirl chamber aligned on the longitudinal axis with the swirl chamber having an internal cylindrical sidewall spaced from the external sidewall of the nozzle to define a first annular region there between. The streamlined swirl chamber includes at least one tangential injection port formed in the internal sidewall thereof for tangentially directing liquid from the first annular region into the swirl chamber along at least a portion of the longitudinal axis.

For ease in understanding the invention, provided below is a description of the physical phenomena occurring in a vortex, which phenomena are utilized with the apparatus and method of the present invention.

The pressure drop at the center of a vortex flow is a direct function of the vortex strength, $\Gamma$, and of the radius of the vortex viscous core, a. The flow field of a rotating fluid or vortex, can be considered with reasonable accuracy to be composed of two regions. In the innermost region, or radius a, the fluid viscosity is predominant, and the fluid rotates en masse as a solid body. In that region the tangential velocity of the fluid increases linearly with the distance from the vortex axis where the tangential velocity is zero. At a distance r from the vortex axis the tangential velocity in this viscous region can be related to the angular velocity, $\Omega$, by the relation:

$$v_1 = \Omega r. \tag{1}$$

This linear relationship is depicted graphically at the top of FIG. 1.

In the outermost region of the vortex the flow is that of an ideal inviscid fluid. In that region, the circulation, which is equal to the integral of the velocity along a closed line encircling the vortex center, is everywhere constant and equal to the vortex strength, $\Gamma$. The velocity at a point located at a distance r from the vortex center in this outermost region is related to $\Gamma$ by $$V_2 = \frac{\Gamma}{2\pi r}. \tag{2}$$

The two expressions (1) and (2) for the velocity give the same value at the idealized location, r=a, of transition between the viscous and inviscid regions. This gives the following relationship between the vortex strength, $\Gamma$, the core radius, a, and the angular velocity, $\Omega$:

$$\Gamma = 2\pi\Omega a^2. \tag{3}$$

Now, if $p_o$ is the ambient pressure away from the vortex center, the pressure at the vortex center, $p_c$, can be determined knowing $\Gamma$, and the liquid density, $\rho$. By applying Bernoulli's equation in the inviscid region and solving the equations of conservation of mass and momentum in the viscous region one finds:

$$p_c = p_o - \rho(\Gamma/2\pi a)^2. \tag{4}$$

This expression is essential to evaluate the pressure drop and the degree of cavitation in the method and apparatus of the present invention. Cavitation at and around the vortex center occurs when $p_c$ drops below the vapor pressure of the liquid, $p_v$, at the considered temperature. In order to increase the pressure drop or the degree of cavitation from Equation (4) it is necessary to either increase the vortex strength, $\Gamma$, or decrease the viscous core size, a.

In one embodiment of the method and apparatus of the present invention, as will be described in detail later, a swirling vortex is generated by tangentially directing fluid about the longitudinal axis of a cylindrical swirl chamber positioned within a nozzle. If $V_t$ is defined as the fluid tangential injection velocity into the swirl chamber, and $D_1$ is the diameter of the swirl chamber, $\Gamma$ is directly related to $V_t$ and $D_1$ by the simple relation:

$$\Gamma = \pi D_1 V_t. \tag{5}$$

Since $D_1$ is a fixed geometric dimension of the swirl chamber, $V_t$ can be varied and is directly determined by the total tangential flow rate, $Q_t$ and the total tangential injection area, $A_t$ with the following relation:

$$V_t = Q_t/A_t. \tag{6}$$

Assuming, in a first embodiment of the present invention, the tangentially injected flow rate, $Q_t$, is the total flow rate into the swirl chamber and out of the nozzle, the axial velocity component of the liquid jet issuing from the nozzle has, in the absence of cavitation, an average value, $V_a$, directly related to $Q_t$ and the area, $A_o$, of a first exit orifice from the nozzle, by the relation:

$$V_a = Q_t/A_o. \tag{7}$$

If desired, $V_a$ can be increased by direct injection of fluid in the axial direction into the nozzle along the longitudinal axis thereof. In this case, $Q_a$, being the axially injected flow rate, $V_a$ is increased to the value:

$$V_a = (Q_t + Q_a)/A_o. \tag{8}$$

For simplicity sake, consider only the case where the total flow rate is limited to $Q_t$. In the absence of cavition, the ratio between the axial and the tangential velocity is directly determined by the nozzle geometry:

$$V_a/V_t = A_t/A_o. \tag{9}$$

This relationship remains valid as long as the pressure $p_c$ (Equation 4) does not drop below the vapor pressure of the liquid. However, if $p_c$ tails below the vapor pressure of the liquid because of either a drop in ambient pressure, $p_o$, away from the vortex, which may be created with an increase in the velocity away from the vortex, or an increase in $\Gamma$ caused by an increase of $V_t$ (Equation 5), then an elongated cavity comprised of cavitation pockets will form substantially on the nozzle longitudinal axis which can significantly reduce the effective exit area of the exit orifice. This induces for a fixed total liquid flow rate into the nozzle an increase in the axial jet velocity $V_a$. The area of the cavity, $A_c$, can be approximated by determining the radius of the cavity, $a_c$, where the pressure is equal to $p_v$. The following relation is obtained by using an equation similar to Equation 4:

$$A_c = \pi a_c^2 = \frac{\Gamma^2}{8\pi} \times \frac{\rho}{(p_o - p_v)}. \tag{10}$$

In the presence of a cavity of cross section area $A_c$ in the plane of the first exit orifice of area $A_o$, the relative axial velocity is increased to become:

$$\frac{V_a}{V_t} = \frac{A_t}{A_o - A_c}. \tag{11}$$

Combining Equations (10), (11), and (5) provides a nonlinear relationship between $V_a$, $V_t$, and the nozzle geometric characteristics as shown below:

$$\frac{V_a}{V_t} = \frac{A_t/A_o}{1 - (A_1/A_o) \times \rho V_t^2 / [2(p_o - p_v)]}, \tag{12}$$

where $A_1 = D_1^2/4$ and is equal to the cross sectional area of the swirl chamber.

Preferably, with each of the embodiments of the swirling jet apparatus useful in the present invention as broadly described herein, the exit orifice and the swirl chamber each have a predetermined diameter, and the tangential injection port in the swirl chamber has a predetermined cross-sectional area selected in accordance with the diameter of the first exit orifice and the diameter of the swirl chamber to control the strength of the vortex formed in the swirl chamber thereby selectively inducing the formation and growth of cavitation pockets in the vortex.

Preferably, large cavity surface areas and surface area to volume ratios are employed and result in higher efficiencies. This can be explained by the need to bring molecules of the compound to be oxidized into close contact with the hydroxyl radicals, or to bring the inclusions to be eliminated into closer contact with the bubble generated high pressure and temperature regions. Since these radicals are generated by bubble collapse, the greater the bubble surface area in contact with the contaminated liquid, the greater the probability of the radicals and contaminants being close enough to combine.

The preferred embodiments of swirling jet nozzles useful in the present decontamination invention will now be described in detail with reference to FIGS. 2–9, wherein like reference numerals refer to like elements throughout the drawings.

In a first embodiment of a nozzle useful in the method of the present invention, shown in FIG. 2, there is provided a nozzle generally referred to as 10 having an inlet port 12 and an external cylindrical sidewall 14 having a longitudinal center axis 16 there through. A first endwall 18 extends inwardly from a distal end portion 20 of external cylindrical sidewall 14.

In accordance with the present invention nozzle 10 further includes chamber means or swirling the liquid entering the nozzle about the longitudinal axis to form a central vortex having a core pressure lower than the vapor pressure of the liquid to induce cavitation pockets in the vortex. As embodied herein, the chamber means includes a hollow streamlined swirl chamber 22 positioned downstream of inlet port 12 within external sidewall 14 of nozzle 10. Swirl chamber 22 has an overall length $L_1$ and includes a streamlined upstream portion 24 positioned proximate inlet port 12, and an internal cylindrical sidewall 26. Internal sidewall 26 of swirl chamber 22 is spaced from external sidewall 14 of nozzle 10 to define a first annular region 28 there between.

By way of example and not limitation, swirl chamber 24 may be aligned on longitudinal axis 16 and held in position within nozzle 10 by streamlined supports 30 which extend transversely between external sidewall 14 and internal sidewall 26. Internal sidewall 26 of swirl chamber 22 preferably extends substantially perpendicularly from endwall 18 of nozzle 10.

In a first embodiment of the present invention as depicted in FIG. 2, a first exit orifice 32 is configured in first endwall 18 and is aligned on longitudinal axis 16 in flow communication with the interior of swirl chamber 22.

The configuration of swirl chamber 22 will now be described in greater detail with reference to FIG. 3 which is a cross section of nozzle 10 taken along lines 3—3 in FIG. 2. In the preferred embodiments of the present invention swirl chamber 22 is configured with a plurality of tangential injection ports 40 extending through internal sidewall 26. Tangential injection ports 40 extend along at least a portion of longitudinal axis 16 in internal sidewall 26. In the preferred embodiment of the present invention tangential injection ports 40 extend along a length $L_4$ of longitudinal axis 16 and have width $W_1$ to define a cross-sectional inlet area of each tangential injection port equal to $L_4 \times W_1$.

The tangential injection ports may also be configured as $n_i$ tangential inlet orifices having a diameter $d_w$. The injection area is then $A_t = n_i \pi d_w^2 / 4$.

Fluid under pressure is directed through inlet port 12 of nozzle 10 as depicted by arrows 42 in FIG. 2, and flows around upstream portion 24 of swirl chamber 22 into annular region 28 between internal sidewall 26 and external sidewall 14. The fluid directed through inlet port 12 has a predetermined pressure which forces the fluid through tangential inlet ports 40 from first annular region 28 into a hollow center 44 of swirl chamber 22. The configuration of tangential inlet ports 40 directs the entering fluid to swirl in a vortex within hollow center 44 of swirl chamber 22 as shown by arrows 46 in FIGS. 2 and 3.

In a further embodiment of the present invention, and as illustrated in FIG. 2, the upstream portion of the swirl chamber may be configured with an inlet orifice 64 of diameter $D_5$ which allows a portion of the inlet flow to enter the swirl chamber axially to thereby increase the axial flow velocity of the liquid passing through and emerging from nozzle 10.

Figure 3:
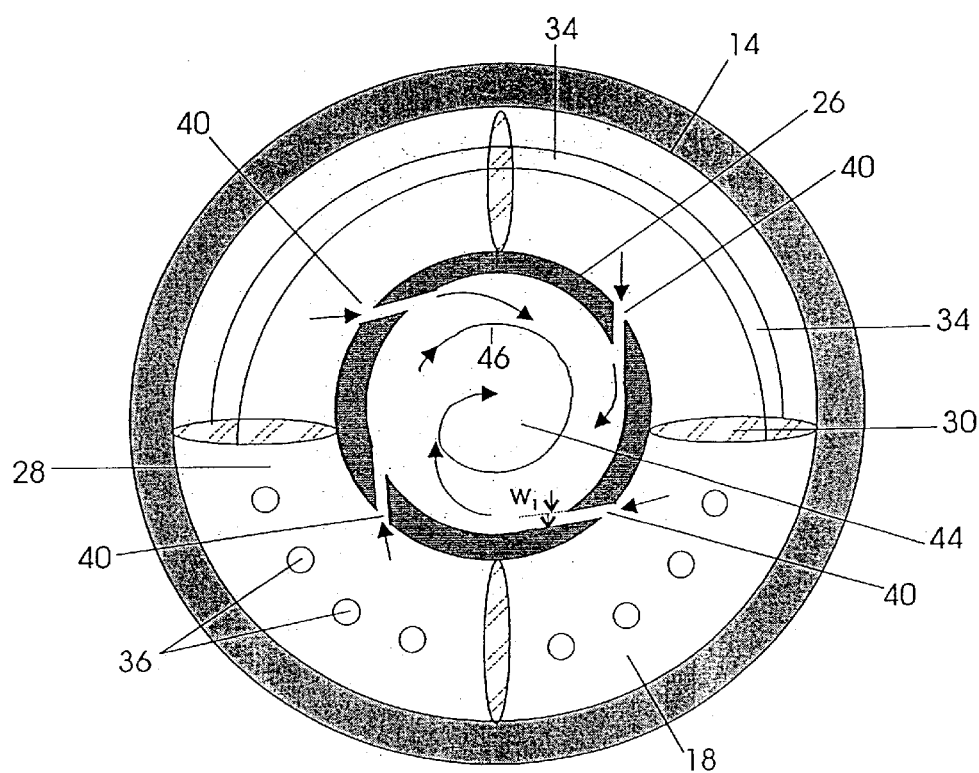
FIG. 3 is a cross-sectional view of the nozzle of FIGS. 2, 4, 5 and 6 taken along the lines III—III of FIGS. 2, 4, 5, and 6.

In a further embodiment of the present invention and as depicted in FIGS. 2 and 3, first endwall 18 may be configured with exit port means therein for sheathing the swirling fluid exiting from the nozzle in an annulus of axially flowing fluid. As embodied herein, the exit port means may comprise an annular slit or opening 34 in first endwall 18. Alternatively, the exit port means may comprise a plurality of circular or noncircular orifices 36 extending through first endwall 18. In either embodiment of the exit port means, a portion of the fluid entering nozzle 10 through inlet port 12 passes through first annular region 28 and is ejected through opening 34 or orifices 36. The fluid emerging from opening 34 or orifices 36 flows axially relative to longitudinal axis 16 in a sheath surrounding the swirling vortex emerging from first exit orifice 32. This annular sheath of axially flowing liquid has the effect of propelling the cavitation pockets in the vortex further from exit orifice 32 before they collapse.

In accordance with the present invention, the strength of the vortex within hollow center 44 of swirl chamber 22 may be adjusted by selectively adjusting the tangential inlet velocity $V_t$ through tangential inlet ports 40. Since, for a given flow rate, the velocity through tangential inlet ports 40 is inversely proportional to the cross-sectional area $A_t$ of the tangential inlet ports, and in the present embodiment all flow through tangential inlet ports 40 into hollow center 44 of swirl chamber 22 must eventually exit through first exit port 32 which communicates with the hollow center 44 of swirl chamber 22, the strength of the vortex is directly proportional to the diameter $D_1$ of the swirl chamber and hence the degree of cavitation in the vortex is controlled by selecting the cross-sectional area of tangential inlet ports 40 in accordance with diameter $D_1$ of the swirl chamber and a diameter $D_2$ of first exit orifice 32.

Figure 4:
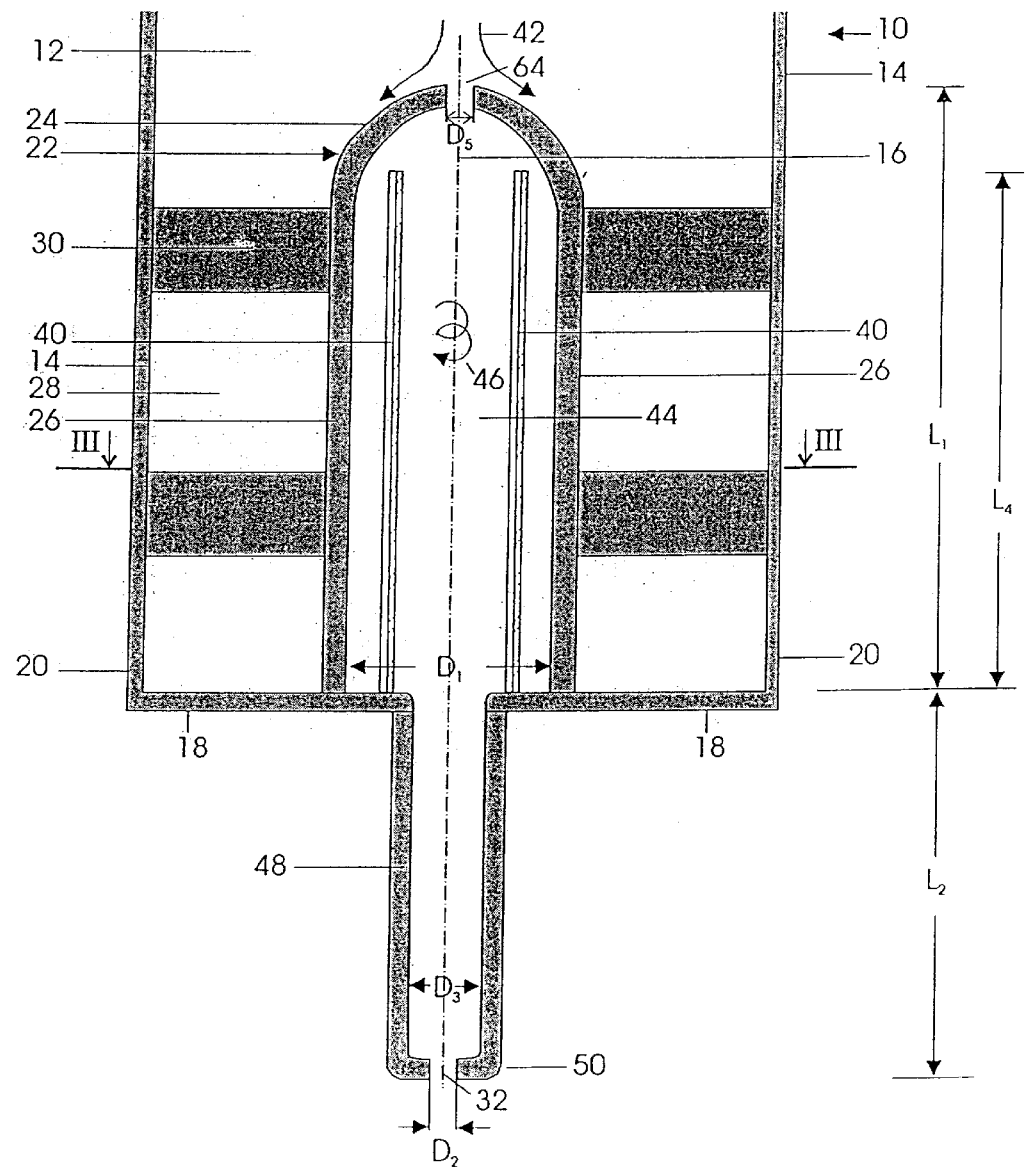
FIG. 4 is a cutaway side view of a second embodiment of a nozzle incorporating the teachings of the present invention.

In a second embodiment of a swirling jet nozzle useful in the present invention, illustrated in FIG. 4, nozzle 10 may further be configured with a feed tube 48 aligned on longitudinal axis 16 and extending from first endwall 18 in flow communication with swirl chamber 22. Feed tube 48 includes a distal end portion 50 spaced from first endwall 18 by a predetermined length $L_2$.

In this second embodiment, first exit orifice 32 is formed in distal end portion 50 of feed tube 48 and has a diameter $D_2$. Feed tube 48 is configured with an internal diameter $D_3$. The vortical flow created in hollow center 44 of swirl chamber 22 flows axially along longitudinal axis 16 from swirl chamber 22 into feed tube 48 and is ejected through first exit orifice 32. The length $L_2$ and diameter $D_3$ of feed tube 48 may be selected to induce acoustic resonance of the flow of the swirling liquid through feed tube 48.

Acoustic resonance can be achieved in nozzle feed-tube 48 when a standing wave forms in the "organ-pipe" section comprised of feed-tube 48. This section is created by the upstream contraction, $(D_1/D_3)^2$ and the nozzle contraction $(D_3/D_2)^2$. Peak resonance will occur when the fundamental frequency of the organ-pipe is near the preferred jet structuring frequency. The exact resonance frequency is dependent on the contractions at each end of the organ pipe; for instance, if both $(D_1/D_3)^2$ and $(D_3/D_2)^2$ are large, then the first mode resonance in the pipe will occur when the sound wavelength in the fluid is approximately four times $L_2$. When $D_3/D_2$ is close to one, resonance occurs when the wavelength is approximately two times $L_2$. Acoustic analysis and experimentation have lead to the following approximation, useful for estimating the length of the organ pipe to induce acoustic resonance:

$$L_2/D_2 \approx K_n/MS_d(1+\beta) \quad (13)$$

where the "mode parameter" $K_n$ is determined, for $D_1/D_3>1$, by $$K=func(n,D/d,M) \approx (2n-1)/4; \text{ for } D_3/D_2>1/\sqrt{M}, \text{ and} \quad (14)$$

$$K_n=func(n,D/d,M) \approx n/2; \text{ for } D_3/D_2<1/\sqrt{M}. \quad (15)$$

In these expressions, n is the mode number of the organ pipe, $S_d$ the critical Strouhal number defined as $S_d=f\,D_2/V_2$, f is the oscillation frequency, M is the Mach number (ratio of jet velocity to sound speed), and β is an end correction for the organ pipe length.

Producing self resonance in the flow through feed tube 48 will have the advantage of combining axial vortex cavitation with axisymmetric cavitation pockets in the shear layer of the fluid exiting from nozzle 10. The natural tendency of a submerged jet to structure into ring vortices when $S_d$ matches 0.3, or a whole number multiple thereof, is enhanced by the self-resonance in the organ pipe feed tube section 48. Cavitation then concentrates into discrete bubble ring vortices located in the shear zone between the issuing jet of diameter $D_2$ and the surrounding ambient fluid. These ring cavities will add to the remediation effectiveness of the linear axial central vortex issuing from exit orifice 32.

Figure 5:
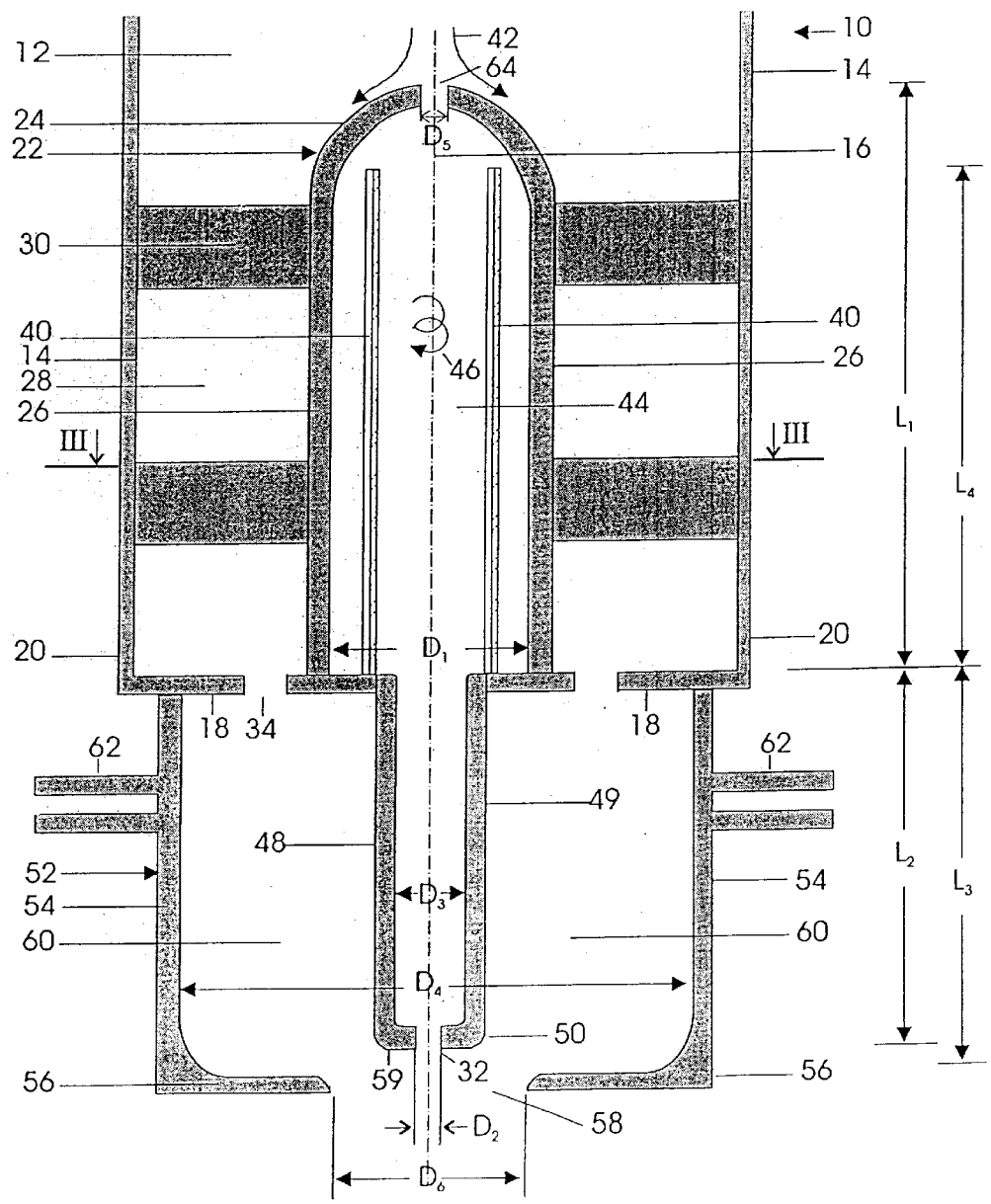
FIG. 5 is a cutaway side view of a third embodiment of a nozzle incorporating the teachings of the present invention.

In a third embodiment of a swirling jet nozzle useful in the present invention, illustrated in FIG. 5, nozzle 10 further includes a shroud tube 52 having a cylindrical sidewall 54 which extends from first endwall 18 of nozzle 10. Shroud tube 52 has a diameter $D_4$ and includes a second endwall 56 extending inwardly from the distal end of cylindrical sidewall 54. Second endwall 56 has a second exit orifice 58, having a diameter $D_6$, configured therein and aligned on longitudinal axis 16.

Second endwall 56 of shroud tube 54 is spaced from first endwall 18 of nozzle 10 a distance $L_3$. Sidewall 54 of shroud tube 52 is spaced from sidewall 49 of feed tube 48 to define a second annular region 60 therebetween. A portion of the fluid flowing into nozzle 10 through inlet port 12 is directed axially from first annular region 28 through exit slit 34 into second annular region 60, and flows from second annular region 60 through second exit orifice 58 to sheath the swirling flow of liquid from first exit orifice 32 in an annular column of axially flowing liquid. In this manner, the swirling vortex exiting from the first exit orifice 32, and having the cavitation pockets formed therein, may be further propelled from second exit orifice 58 by the axially flowing sheath of fluid before the cavitation pockets collapse.

Figure 6:
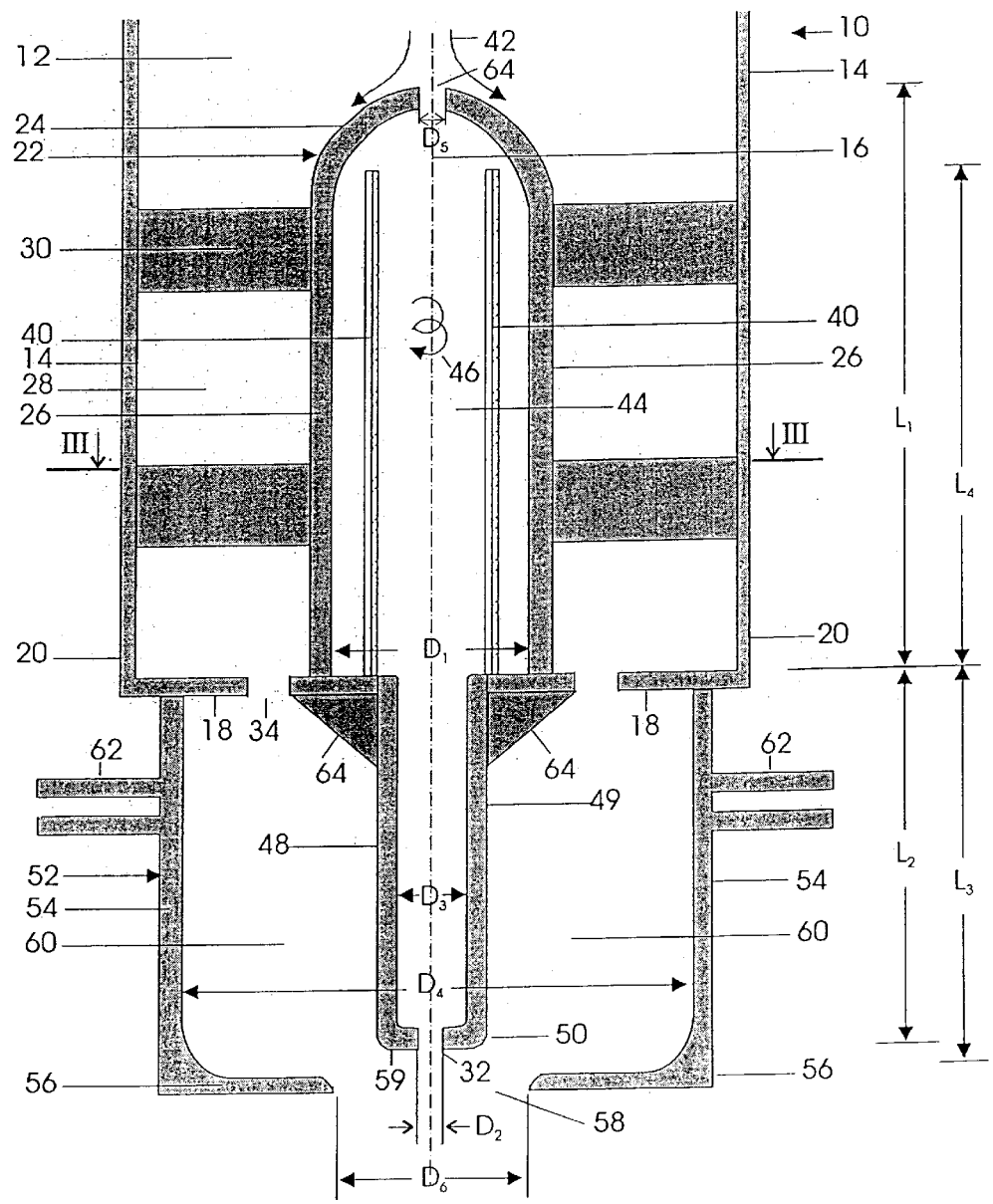
FIG. 6 is a cutaway side view of a fourth embodiment of a nozzle incorporating the teachings of the present invention.

Second exit orifice 58 may be disposed at the same position as first exit orifice 32, i.e., $L_2=L_3$, if the outside wall of feed tube 48 is streamlined along at least a portion of its length. By way of example and not limitation, such streamlining may be accomplished by configuring the outside walls of feed tube 48 with an inclined surface 64 as shown in FIG. 6. Such streamlining enables a smooth transition without separation between the fluid flow from second annular region 60, and the fluid flow in the central vortex exiting feed tube 48, as both exit from orifice 58. This smooth transition can be achieved more easily if exit orifices 58 and 32 are spaced from one another, the spacing being determined for optimum mixing dynamics, i.e., without separation of the fluid flows. Inclined surface 64 also provides the advantage of reducing pressure losses in the expansion region behind orifices or slots 34.

Shroud tube 54 may be further configured with inlet port means for directing fluids such as air or liquid into second annular region 60. As embodied herein, the inlet port means includes inlet ports 62. Fluid directed through inlet ports 62 flows through second annular region 60 and out of second exit orifice 58 to sheath the swirling liquid exiting through first exit orifice 32 in an annulus of axially flowing fluid. The fluid injected through inlet ports 62 may be either a liquid or a gas, each of which will emerge through second exit orifice 58 to sheath the swirling liquid exiting through first exit orifice 32 in an annulus of axially flowing fluid.

Figure 7:
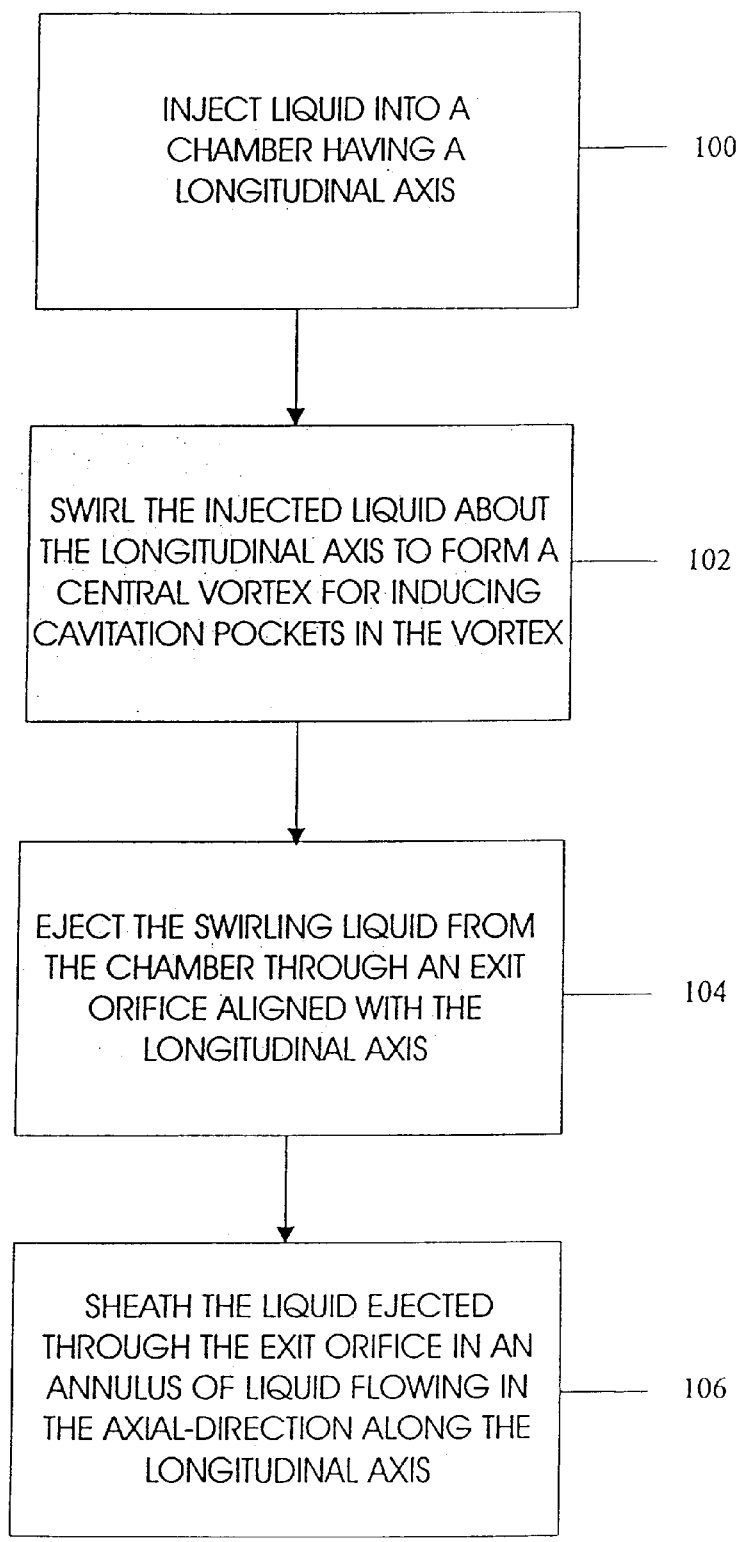
FIG. 7 is a flow chart illustrating the steps of the method of one embodiment of the present invention.

Embodiments of nozzles incorporating the teachings of the present invention have been described above with references to FIGS. 2–6. The present invention also provides a method for forming a cavitating liquid jet, the steps of the method being incorporated in the embodiments of the present invention described hereinabove. With reference to FIG. 7, the steps of the method of the present invention are illustrated in the form of a flowchart. As embodied herein, the present invention provides a method for forming a cavitating liquid jet wherein at step 100, liquid is injected into a chamber having a longitudinal axis. At step 102 the injected liquid is swirled about the longitudinal axis of the chamber to form a central vortex having a core pressure lower than the vapor pressure of the injected liquid to thus induce cavitation pockets in the vortex. Preferably, the liquid is swirled about the longitudinal axis of the chamber by directing the liquid tangentially into the chamber along at least a portion of the longitudinal axis.

Next, at step 104 the swirling liquid within the chamber is ejected through an exit orifice aligned on the longitudinal axis of the chamber. In this manner, the cavitation pockets formed in the central vortex are also injected through the exit orifice and may be directed towards a wall or surface spaced to create a short gap between the nozzle and the surface. The exiting swirling fluid jets stagnate within this gap, increasing ambient pressure in that region. The changing pressure initiating the asymmetric collapse of the cavitation bubble. One portion of the bubble wall begins to dimple, and the pressure differences create a microjet, or reentrant jet, which accelerates collapse of the bubble. The microject travels through and impinges on the opposite wall of the collapsing bubble, resulting in a collapse with a violent force that may be advantageously used for water purification as described above. It will be appreciated that the geometry of the surface is not critical to the invention and that it may be substituted with plates or walls of other geometry, provided that it is in sufficient proximity to the swirling jet nozzles to enhance the cavitation as described above. The surface may contain orifices to control the pressure in the gap.

In a further embodiment of the method of the present invention, and as illustrated at step 106 in FIG. 7, the swirling liquid ejected through the exit orifice may be sheathed in an annulus of liquid flowing axially along the longitudinal axis. Sheathing the swirling vortex and cavitation pockets formed therein in an annulus of axially flowing liquid provides the advantage of propelling the swirling vortex and cavitation pockets further away from the exit orifice prior to collapse of the cavitation pockets. In this manner, the surface toward which the swirling vortex and cavitation pockets are directed may be spaced further from the exit orifice thus extending the time in which cavitation is present while still advantageously utilizing the violent collapse of the cavitation pockets.

Figure 8:
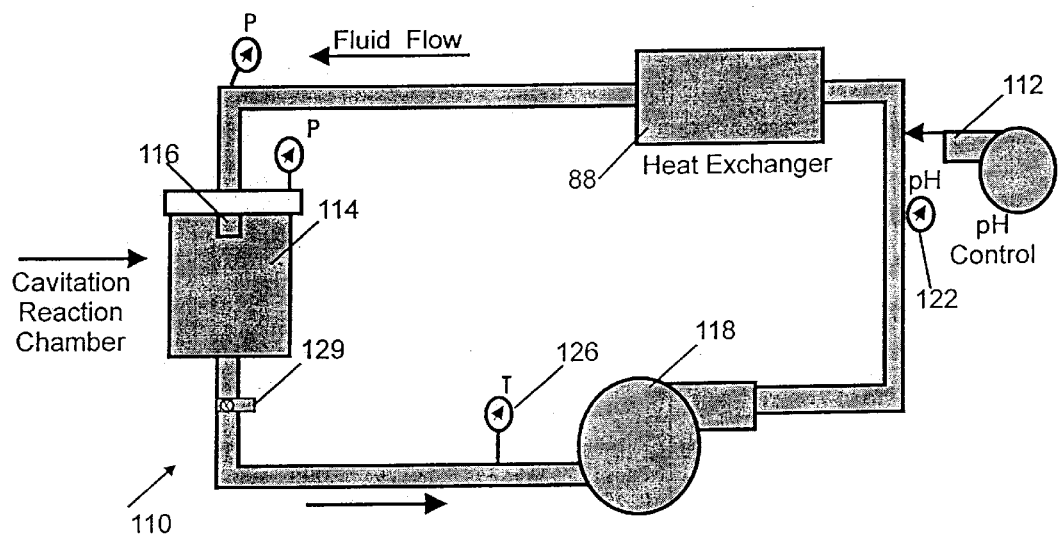
FIG. 8 is a flow diagram of one embodiment of a system that can be operated in a batch mode and that employs the present invention using swirling cavitating jets.

A batch process embodiment of the present invention is shown generally in FIG. 8. Circulating flow loop 110 comprises cavitation reaction chamber 114 in which the circulating fluid is caused to flow through jet nozzle 116. The circulating fluid is driven by main liquid pump 118. Circulating flow loop 110 includes pH sensing means 122 for measuring the pH of the circulating fluid, and also includes pH control means 124 for adjusting the pH of the liquid (for example, by injection of concentrated acid or base solutions into the circulating fluid). Circulating flow loop 110 also contains temperature sensor means 126 for measuring the temperature of the liquid. The desired temperature of the liquid can be maintained by passage through heat exchanger 128. Alternatively, separate chillers and/or heaters, or other convenient temperature control means, may be employed as convenient. Cavitation reaction chamber 114 consists of a sealed chamber which may be operated at a moderately elevated pressure in which one or more swirling jet flows are produced, for example by one or more of the nozzles of the configurations of FIGS. 2 through 6. Contaminated liquid can be circulated through circulating flow loop 110 for a predetermined treatment cycle, or until the contaminants have been reduced to target levels. Sampling port 129 permits assays of the treated fluid to determine the duration of the treatment cycle.

Figure 9:
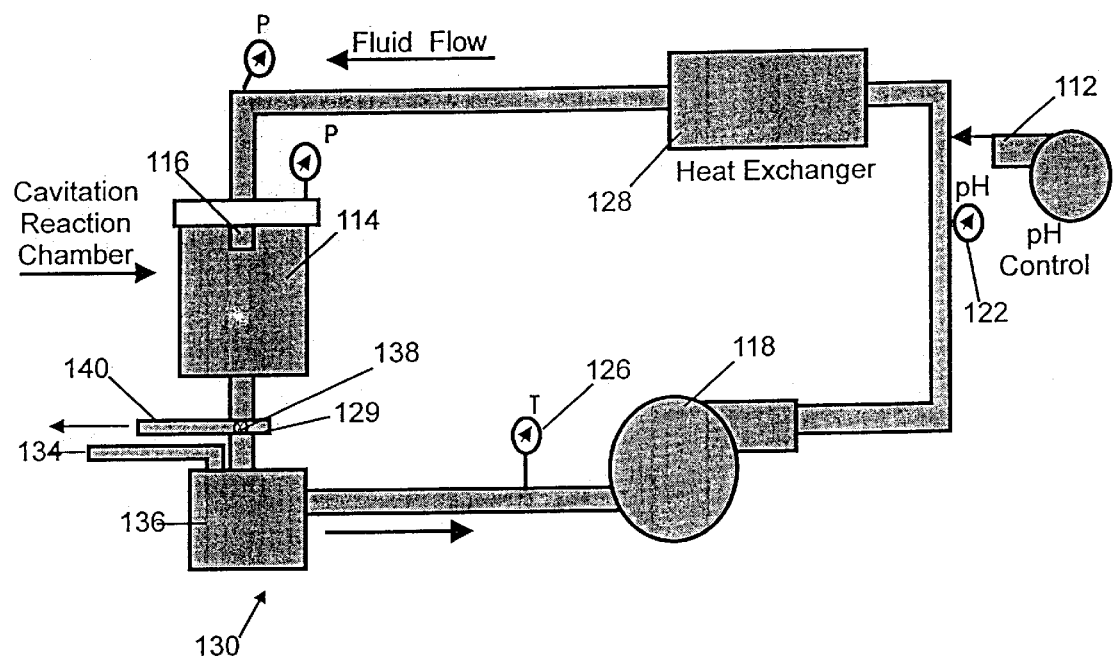
FIG. 9 is a flow diagram of one embodiment of a system that can be operated in a continuous flow mode and that employs the present invention using swirling cavitating jets.

The present invention is well suited to operation in a continuous decontamination system, one embodiment of which is shown in FIG. 9. Decontamination system 130 includes feed reservoir 136 for receiving the flow of contaminated liquid through feed pipe 134, as well as optionally receiving partially treated liquid from cavitation reaction chamber 114 via recycle valve 138. Cavitation reaction chamber 114 consists of a sealed chamber which may be operated at a moderately elevated pressure in which one or more swirling jet flows are produced, for example by one or more of the nozzles of the configurations of FIGS. 2 through 6. Sampling port 129 permits assays of the treated fluid in order to adjust the amount of the recycle flow. Adjustment of the amount of the recycle flow determines the mean residence time of the fluid in cavitation reaction chamber 114. Recycle valve 138 enables treated liquid exiting cavitation reaction chamber 114 to be recycled into feed reservoir 136 for further treatment or to be removed from decontamination system 130 via outflow pipe 140.

The relative pressures may be adjusted to optimize the cavitation. For example, when operating at approximately atmospheric ambient pressures, it is preferred that the liquid in manifold 11 be pressurized to at least about 60 psi above the pressure of the liquid in outer chamber 114; at higher ambient pressures, the preferred pressure differential will be greater. It will be within the skill of the operator to adjust the system to achieve optimal cavitation. As fluid is jetted through the nozzles, swirling jet cavitation is induced and the contaminants are decomposed.

A decontamination system of the present invention may utilize a multi-chamber configuration, so that multiple swirling jets act on the liquid to be decontaminated. The chambers may be arrayed in parallel, or may be arrayed sequentially, so that a given volume of liquid passes through, and is treated by, multiple swirling jet nozzles. For example, a decontamination system may employ a series of stages or chambers through which the flow sequentially progresses through one or more swirling jet nozzles, and in which the ambient pressures in the various chambers are controlled and decrease in the direction of flow such that a desired set of cavitation numbers is achieved. Stagnation plates or surfaces may be included in one or more of the chambers.

The physical and chemical cavitation reactions employed in this invention will be effective for removing or reducing a variety of contaminants from aqueous and non-aqueous liquids. Frequently, all contaminating compounds will not have been identified in the liquid needing treatment. However, the aggressive cavitation-induced oxidation generated in the manner described here is expected to be useful for causing oxidation of most organic compounds, and oxidation or reduction of some inorganic compounds as well. Oxidation of organic contaminants is a particularly attractive treatment since the contaminants are readily oxidized to carbon dioxide, water and other harmless compounds.

A wide variety of liquids and water sources may be contaminated with various organic wastes and/or dissolved organic compounds. It is expected that decontamination systems utilizing the jet cavitation of the present invention will be advantageous in remediating such liquids and water sources. In addition to eliminating dissolved contaminants, the present system can also eliminate undesirable microorganisms (including various algae (both unicellular and multicellular), bacteria, fungi, protozoa, and viruses) as well as larvae. Pathogenic microorganisms, including, but not limited to, bacteria such as *E. Coli* and *salmonella*, both of which cause gastrointestinal illness, are a source of contamination to be eliminated from municipal water supplies, private wells, and other waters. Remediation may be desired to eliminate algae, fungi, protozoa, or viruses in a variety of settings. Aqueous solutions containing any of these microorganisms can be subjected to the fluid jet cavitation described herein, resulting in their destruction and decomposition.

Other organisms may be vulnerable to treatment by the present cavitation process when present in their larval form. For example, Zebra mussels, small, fingernail-sized, freshwater mollusks accidentally introduced to North America, have rapidly spread throughout the Great Lakes, Mississippi River basin and other inland waterways in the United States and Canada. A major nuisance, Zebra mussels have colonized water supply pipes of hydroelectric and nuclear power plants, public water supply plants, and industrial facilities, in many cases dangerously restricting water intake to heat exchangers, cooling systems and the like. Although the adult mussel would not be affected, the larval form is free-swimming and susceptible to destruction by fluid jet cavitation. Thus, it may be promising to treat large volumes of waters where zebra mussels are problematic, to eliminate significant larval populations before they colonize additional surfaces. The method can be similarly applied to larval forms of other pests which may be present in water.

The range of application for the remediation process and systems of this invention is almost limitless. For example, systems and apparatuses incorporating the fluid jet cavitation remediation described herein can be adapted to the full range of municipal and industrial settings, including, but not limited to treatment of navigable waters, sanitary systems and industrial effluent. In addition, smaller systems and units will be suitable for the remediation needs of smaller-scale applications, including, but not limited to, the treatment of private wells and pools, the prevention of disease and system upset in aquaculture and aquarium environments, and the like.

It has been further found that controlling the liquid and cavitation environment can further increase oxidation efficiency. The temperature and pH of the liquid to be treated can be controlled to increase the efficiency of the decontamination. In addition, treating the liquid by entraining or saturating with various gases, preferably prior to cavitation, can be employed to further improve the rate of decontamination. Suitable gases include, but are not limited to, ozone, argon, krypton, helium and oxygen. In general, however, it is believed that optimization will depend on the nature of the liquid and the contaminants.

The remediation of the present invention can also be optimized through control of the cavitation number. Again, this is believed to be linked to the contaminant sought to be decomposed, and will vary among applications of the invention. "Cavitation number" is the ratio of the local ambient pressure of the liquid into which the fluid jet issues to the pressure drop across the nozzle. The cavitation number can be controlled by adjusting the pressure of the various reservoirs or chambers through which the liquid travels, that is, the incoming pressure entering the jet nozzle and/or the ambient pressure of the liquid in which the nozzle exit port is submerged.

The efficient decontamination process of this invention also benefits from the fact that pumps are quite efficient in converting electric (or other) power into hydraulic power, which is really all that is needed to drive the remediation embodiments and systems disclosed here. This technology can be used in a variety of systems for treating polluted water, groundwater, wastewater, industrial process liquids, and drinking water. Swirling fluid jet cavitation remediation can be employed as a simple stand-alone process or as a part of a more complex treatment train. In certain applications, it may be desirable to include optional additional processing steps in the decontamination system. For example, the treated liquid may be further subjected to filtration, ion exchange, ultraviolet radiation, or other chemical or physical means for further purification. The remediation process of this invention may be used in a large-scale fixed treatment site or as a small-scale temporary or portable remediation system.

EXAMPLES

Example 1

This example examines the use of the swirling jet nozzles of this invention to generate cavitation-induced oxidation of reagent grade p-nitrophenol (PNP) (Aldrich, 99%). The PNP was in crystalline form and was mixed with distilled water to an initial concentration of 8 ppm. PNP concentrations were measured using a UV-Vis spectrophotometer by standard procedures. The spectrophotometer was calibrated against known concentrations of PNP in distilled water at a wavelength of 400 nm after shifting the sample pH to 11 by the addition of NaOH to enable measurement employing the absorption band at 400 nm. Oxidation efficiency is reported as the amount of PNP removed (in milligrams) per unit input energy (in megajoules). The unit input energy is the product of pressure, flow rate and time.

A stainless steel jet cavitation reactor of the general configuration illustrated in FIG. 2 was utilized. The inside diameter of inlet port 12 was 1.07 in. The swirl chamber 22 had a length $L_1$ of 4.3 in. and included three tangential injection ports 40 of length $L_4$=2.2 in. and width $W_1$=0.035 in. The inside diameter $D_1$ of swirl chamber 22 was $D_1$=0.5 in. and exit orifice 32 had a diameter $D_2$=0.5 in. The test solution was maintained at pH=3.8, temperature=107 deg.F (42 deg.C). The local ambient pressure of the liquid reservoir outside the nozzle was atmospheric. The pressure entering the nozzles was 58 psi. The flow rate was 25 gpm. During testing, 3 ml samples were drawn from the test reservoir each hour for measurement of PNP concentration. Results are reported in Table I.

The oxidation efficiency of the swirling jet cavitation of this example was compared to that of ultrasonic cavitation, using a magnetostrictive ultrasonic horn under the same conditions. The ultrasonic experiment was conducted at 107 deg.F (42 deg.C) and also at 77 deg.F (25 deg.C) (which we found to be a more efficient temperature for ultrasonic cavitation). Measurements were taken after 4 hours. Results are reported in Table I.

TABLE I

| Experiment | % PNP Removed | Duration | Oxidation Efficiency |
|---|---|---|---|
| Swirling Jet (107 F) | 68% | 1 hour | 15.6 mg/MJ |
| Swirling Jet (107 F) | 88% | 2 hours | 10.1 mg/MJ |
| Swirling Jet (107 F) | 94% | 3 hours | 7.20 mg/MJ |
| Ultrasonic (107 F) | 4% | 4 hours | 0.05 mg/MJ |
| Ultrasonic (77 F) | 13% | 4 hours | 0.23 mg/MJ |

As can be seen, the oxidation efficiency (amount of PNP removed per unit input energy) was greatly improved with the swirling jet cavitation of the present invention.

Although specific embodiments of the invention are described here, it should be understood that such embodiments are by way of example only and illustrate only a small number of possible specific embodiments that represent applications of the principles of the invention. Various changes, configurations, modifications and alterations of the teachings of the present invention may be contemplated by those skilled in the art without departing from the intended spirit and scope of the present invention. As such, it is intended that the present invention only be limited by the terms of the appended claims.

What is claimed is:

1. A method for the remediation of contaminated liquid in which said contaminated liquid is pumped through a swirl chamber having a longitudinal axis to form a central vortex about said longitudinal axis, said central vortex having a core pressure lower than the vapor pressure of the liquid for inducing cavitation pockets in the vortex, wherein said cavitation causes decomposition of contaminants in said liquid.

2. The method of claim 1 which further comprises ejecting said liquid through an exit orifice from said swirl chamber into a volume of liquid having a predetermined ambient pressure.

3. The method of claim 2 wherein liquid jetting from said exit orifice into said volume of liquid induces vortical cavities or structures to form.

4. The method of claim 2 wherein said liquid pumped through the swirl chamber has a predetermined pressure, and wherein the swirl chamber is configured with a predetermined length along said longitudinal axis selected in accordance with the predetermined pressure of said liquid and the ambient pressure of the environment into which said liquid is ejected to enhance the formation of cavitation within the swirling vortex in said swirl chamber.

5. The method of claim 1 in which said contaminated liquid is passed through a series of said swirl chambers.

6. The method of claim 1 in which said decomposition is the result of oxidation, or reduction or both.

7. The method of claim 1 in which said decomposition is the result of local heating, mechanical destruction, or both.

8. The method of claim 1 in which said liquid is water or an aqueous solution.

9. The method of claim 1 in which the contaminants in said contaminated liquid are selected from the group consisting of organic compounds, oxidizable inorganic compounds, reducible inorganic compounds, microorganisms and larvae.

10. The method of claim 1 which further comprises the steps of determining the contaminants in said contaminated liquid and controlling the pH of said contaminated liquid to optimize the formation of cavitation pockets and the decomposition of said contaminants.

11. The method of claim 1 which further comprises the steps of determining the contaminants in said contaminated liquid and controlling the temperature of said contaminated liquid to optimize the formation of cavitation pockets and the decomposition of said contaminants.

12. The method of claim 1 which further comprises the step of treating said liquid by ion exchange, adding rare gases to said liquid, treating said liquid by ultraviolet radiation, or recycling at least a portion of said liquid through said swirl chambers.

13. A method for the remediation of contaminated liquid in which said contaminated liquid is pumped through a swirling jet nozzle which comprises:

an inlet port;

an external cylindrical sidewall having a longitudinal axis therethrough;

a first end wall extending inwardly from a distal end of said external cylindrical sidewall, and a first exit orifice aligned on said longitudinal axis; and chamber means, positioned downstream of said inlet port within said external cylindrical sidewall, for swirling liquid about said longitudinal axis to form a central vortex having a core pressure lower than the vapor pressure of the liquid for inducing cavitation pockets in the vortex, wherein said cavitation is sufficient to cause decomposition of contaminants in said liquid.

14. The method of claim 13 in which said chamber means includes a hollow, streamlined swirl chamber aligned on said longitudinal axis, said swirl chamber having an internal cylindrical sidewall spaced from said external sidewall of said nozzle to define a first annular region therebetween; and at least one tangential injection port having a predetermined length extending along said longitudinal axis and having a predetermined width, said tangential injection port formed in said internal sidewall of said swirl chamber for tangentially directing liquid from said first annular region into said swirl chamber along at least a portion of the longitudinal axis.

15. The method of claim 13 for remediating contaminated liquid comprising the step of passing said liquid through one or more swirling jet nozzles to induce swirling fluid jet cavitation in said liquid.

16. An apparatus for the remediation of contaminated liquids by the induction of jet cavitation in said liquid, comprising:

a pump connected to a source of contaminated liquid, means for communicating the pump with an entry chamber for receiving a flow of contaminated liquid, and one or more swirling fluid jet nozzles arrayed at the downstream end of said entry chamber in a manner which allows said contaminated liquid to flow from said entry chamber through said jet nozzles, inducing formation of a central vortex in which cavitation pockets are formed, and then ejected through exit ports in said nozzles, wherein said cavitation is sufficient to cause decomposition of contaminants in said liquid and wherein said central vortex has a core pressure lower than the vapor pressure of the liquid.

17. The apparatus of claim 16 which further comprises an outer chamber immediately downstream of said swirling jet nozzles, said outer chamber containing a volume of liquid sufficient to submerge the exit ports of said nozzles.

18. The apparatus of claim 17 which further comprises an impact surface downstream of and in sufficiently close proximity to said exit ports to cause the cavitation bubbles in the fluid jets exiting said ports to collapse between said exit ports and said surface.

19. The apparatus of claim 18 which further comprises a recycle valve and loop to allow the optional recycle of all or a portion of treated liquid through said swirling jet nozzles.

20. A method for remediating contaminated liquid, comprising the steps of: (a) injecting liquid into a chamber having a longitudinal axis, (b) swirling the injected liquid about the longitudinal axis to form a central vortex having a core pressure lower than the vapor pressure of the injected liquid for inducing cavitation pockets in the vortex, and (c) ejecting the swirling liquid through an exit orifice aligned with the longitudinal axis.

21. The method of claim 20 wherein the injected liquid is directed tangentially into the chamber along at least a portion of the longitudinal axis through at least one tangential injection port having a predetermined length extending along said longitudinal axis and having a predetermined width.

* * * * *

UNITED STATES PATENT AND TRADEMARK OFFICE
Certificate

Patent No. 6,221,260                                                              Patented: April 24, 2001

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Georges L. Chahine, Silver Spring, MD; Kenneth M. Kalumuck, Columbia, MD; and Richard Gregg, II, Huntsville, Alabama Signed and Sealed this Eighth Day of January 2002.

WANDA L. WALKER
*Supervisory Patent Examiner*
Art Unit 1723